United States Patent [19]

Schmidbaur et al.

[11] Patent Number: 4,620,020
[45] Date of Patent: Oct. 28, 1986

[54] BIS-PHOSPHONIUM SALTS AND PROCESS FOR MAKING THEM

[75] Inventors: Hubert Schmidbaur, Garching; Cornelia Dörzbach, Munich, both of Fed. Rep. of Germany; Graham Bowmaker, Auckland, New Zealand

[73] Assignee: Hoecht Aktiengesellschaft, Frankfurt, Fed. Rep. of Germany

[21] Appl. No.: 719,590

[22] Filed: Apr. 4, 1985

[30] Foreign Application Priority Data

Apr. 21, 1984 [DE] Fed. Rep. of Germany ....... 3415037

[51] Int. Cl.$^4$ .............................................. C07F 9/54
[52] U.S. Cl. ......................................... 556/18; 568/2; 568/10
[58] Field of Search ................... 568/2, 10; 556/18

[56] References Cited

U.S. PATENT DOCUMENTS

| | | | |
|---|---|---|---|
| 2,941,008 | 6/1960 | Wagner | 568/2 |
| 2,998,416 | 8/1961 | Mendel | 556/18 X |
| 3,098,878 | 7/1963 | Harris et al. | 568/10 |
| 3,322,861 | 5/1967 | Gillham et al. | 568/10 X |
| 3,345,392 | 10/1967 | Grayson et al. | 556/18 |
| 3,374,256 | 3/1968 | Driscoll et al. | 556/18 |
| 4,209,554 | 6/1980 | Traynor et al. | 568/10 X |
| 4,289,809 | 9/1981 | Traynor et al. | 568/10 X |
| 4,341,714 | 7/1982 | Ellison et al. | 568/2 |

FOREIGN PATENT DOCUMENTS

| | | | |
|---|---|---|---|
| 098296 | 6/1982 | Japan | 568/10 |
| 2101601 | 1/1983 | United Kingdom | 568/10 |

*Primary Examiner*—Helen M. S. Sneed
*Attorney, Agent, or Firm*—Connolly and Hutz

[57] ABSTRACT

Novel bis-phosphonium salts of the general formula

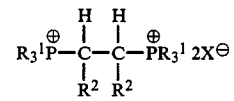

in which $R^1$ stands for a straight or branched alkyl group having from 1 to 12 carbon atoms, $R^2$ stands for methyl, ethyl, n-propyl or iso-propyl, and $X^\ominus$ stands for a monovalent anion or complex anion, or $2\,X^\ominus$ stands for a bivalent inorganic anion, are made.

To this end, a triorganylphosphonium alkylide of the general formula $R_3^1P=CHR^2$ is reacted with an anhydrous copper(II)-halide in a solvent at temperatures of $-78°$ C. to $0°$ C. with agitation, precipitated bis-phosphonium dihalogenocuprate(I) is separated and, if desired, converted by metathesis into another bis-phosphonium salt.

9 Claims, No Drawings

BIS-PHOSPHONIUM SALTS AND PROCESS FOR MAKING THEM

The invention relates to novel bis-phosphonium salts of the general formula

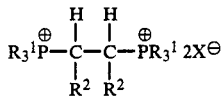

in which
R¹ stands for a straight or branched alkyl group having from 1 to 12 carbon atoms,
R² stands for methyl, ethyl, n-propyl or iso-propyl, and
X$^\ominus$ stands for a monovalent anion or complex anion,
2X$^\ominus$ stands for a bivalent inorganic anion.

In the above general formula, R¹ preferably stands for methyl, ethyl, n-propyl, iso-propyl or butyl and X$^\ominus$ stands for a halide, dihalogenocuprate(I) (CuHal$_2^\ominus$), tetraphenylborate (($C_6H_5$)$_4$B$^\ominus$), tetrafluoroborate (BF$_4^\ominus$) or hexafluorophosphate (PF$_6^\ominus$), or 2X$^\ominus$ stands for a sulfate.

The invention also relates to a process for making bisphosphonium salts of the general formula

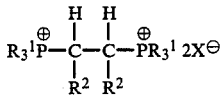

in which
R¹ stands for a straight or branched alkyl radical having from 1–12 carbon atoms, a cycloalkyl having from 5–8 carbon atoms or a substituted or unsubstituted phenyl,
R² stands for a hydrogen radical, methyl, ethyl, n-propyl or iso-propyl, and
X$^\ominus$ stands for a monovalent anion or complex anion, or
2X$^\ominus$ stands for a bivalent inorganic anion,
R¹ standing however for a group other than a cycloalkyl or phenyl group in the event of R² standing for a radical other than a hydrogen radical, which comprises: reacting a triorganylphosphonium alkylide of the general formula R$_3^1$P=CHR² with an anhydrous copper(II)halide in a solvent at temperatures of −78° C. to 0° C. with agitation, separating precipitated bis-phosphonium dihalogenocuprate(I) and, if desired, subjected to metathesis for conversion into another bis-phosphonium salt.

Once again, R¹ preferably stands for methyl, ethyl, n-propyl, iso-propyl or butyl, X$^\ominus$ stands for a halide, a dihalogenocuprate(I) (CuHal$_2^\ominus$), tetraphenylborate (($C_6H_5$)$_4$B$^\ominus$), tetrafluoroborate (BF$_4^\ominus$) or hexafluorophosphate (PF$_6^\ominus$), or 2X$^\ominus$ stands for a sulfate.

Bis-phosphonium salts in the general formula of which R² stands for hydrogen are partially known, e.g. [(CH$_3$)$_3$PCH$_2$CH$_2$P(CH$_3$)$_3$]$^{2+}$ (cf. E. Muetterties et al., Inorg. Chem. 3, page 444 (1964) and [(C$_6$H$_5$)$_3$PCH$_2$CH$_2$P(C$_6$H$_5$)$_3$]$^{2+}$ (cf. G. Wittig et al., Ann. 619, page 10 (1958).

The process of this invention can more particularly be carried out as follows:
(a) a solution of the triorganylphosphonium alkylide in an ether in a molar ratio of alkylide to CuHal$_2$ of at most 1 is slowly added dropwise with intense agitation at temperatures of −78° C. to 0° C., preferably −70° C. to −60° C., to a suspension of an anhydrous Cu(II)-halide in an ether, the whole is allowed to assume room temperature while agitation is continued over a period of several hours, and precipitated bis-phosphonium-dihalogenocuprate(I) is filtered off, washed with water and, if desired, subjected to metathesis for conversion into another bis-phosphonium salt;
(b) tetrahydrofurane, a dioxane or ethyleneglycol ether is used as the ether;
(c) bis-phosphonium-hexafluorophosphate is made by filtering off precipitated bis-phosphonium-dihalogenocuprate(I), washing it with water, dissolving it in concentrated hydrochloric acid, admixing it, while cooling with ice, with an aqueous solution of an alkali metal or ammoniumhexafluorophosphate, filtering off precipitated bis-phosphoniumhexafluorophosphate and washing it with hydrochloric acid and water;
(d) bis-phosphonium-hexafluorophosphate is made by filtering off precipitated bis-phosphonium-dihalogenocuprate(I), washing it with water, dissolving it in acetonitrile, admixing it with hydrogen peroxide if desired, stirring it with admission of air, filtering off precipitated bis-phosphonium-halogenocuprate(II), dissolving it in water while adding hydrochloric acid, admixing it, while cooling with ice, with an aqueous solution of an alkali metal or ammoniumhexafluorophosphate, separating the resulting bis-phosphoniumhexafluorophosphate and washing it with water and hydrochloric acid. The reactions of this invention partially occur in accordance with the following equations, for example:

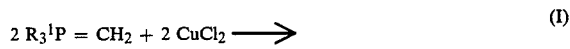

(I)

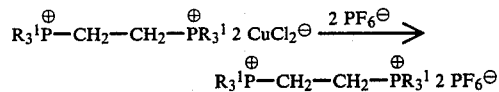

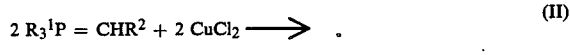

(II)

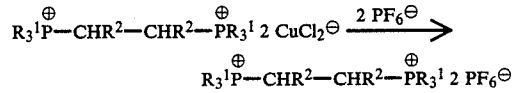

The compounds of this invention are representatives of a class of substances which have recently been gaining increasing interest. In industrial chemistry, phosphonium compounds find increasing use as phase transfer catalyts (cf. E. V. Dehmlow and S. S. Dehmlow, Phase-Transfer-Catalysis, published by Verlag Chemie 1980). Phosphonium salts have also been tried in such encouraging fields as for the production of zeolites (European Specification 0 055 046 A1, where P+-salts are used as "templates", for the thermal stabilization of polyvinyl chloride (Japanese Specification B-82 96 034), for flameproofing polyolefins (Japanese Specification B-79 04944), and also for the conversion of synthesis gas into ethylene. Still further, phosphonium salts are used for catalyzing the reaction of epoxides with phenols or carboxylic acids (U.S. Pat. No. 4,405,766).

The starting materials used in the process of this invention are ylides which are obtainable by known methods in high yields and are easy to isolate as material free from salt (H. Schmidbaur, Inorg. Synth. 18, 135–143 (1978); H. Schmidbaur and W. Tronich, Chem. Ber. 101, 595–603 (1968); R. Köster et al., Liebigs Ann. Chem. 739, 211–219 (1970); H. Schmidbaur et al., Chem. Ber. 105, 1084–1086 (1972)). They are extremely soluble in organic solvents and can therefore be reacted under very mild conditions. The solvents should preferably be selected from those which have an ether function, e.g. dioxanes or glycol ethers. Tetrahydrofurane is a particularly preferred solvent. The dissolved ylide is combined at temperatures of −78° to 0° C., preferably −60° to −70° C. with an anhydrous Cu(II)-halide, the molar ratio of ylide:halide being ≦1. Even in the event of $CuHal_2$ being present in excess, the reaction remains unaffected since $CuHal_2$ is easy to extract from the insoluble reaction product with the aid of water. The primary products, namely bis-phosphonium salts containing 2 equivalents $Cu(I)Hal_2^\ominus$ as an ion of opposite charge, which are obtained in good yields have an anionic portion readily exchangeable in known manner; thus, for example, it is possible to separate the bis-phosphonium salts in form of hexafluorophosphates by subjecting the dichlorocuprate(I) to a metathesis reaction with equivalent quantities of $NH_4(PF_6)$; in this case, it may turn out necessary initially to oxidize $Cu^+$ by means of $H_2O_2$ and/or air in acetonitrile as a solvent to $Cu^{2+}$. Whatever other anion can be introduced by metathesis into the separable bis(phosphonium-hexafluorophosphates).

In the event of a methylide ($R_3{}^1P=CH_2$) being used in the process herein described, bis-phosphonium compounds having ethylene bridges are obtained. In those cases in which a H-radical of the methylide group is replaced by an alkyl group, e.g. $CH_3$ ($R_3{}^1P=CHCH_3$), isomeric compounds are obtained (RR/SS-pair of enantiomers; RS-meso form). As has unexpectedly been found, the diasteromers are not obtained in the statistic ratio as would have been expected (50% RR/SS, 50% RS) but the two optical antipodes are formed in a considerable excess (molar ratio 2.8:1). This unusual distribution of the products can reliably be demonstrated on the evidence of the $\{^1H\}$ $^{13}$-C-NMR-spectrum of the compound of the formula $(C_2H_5)_3P^\ominus-CHCH_3-CHCH_3-P^\ominus(C_2H_5)_3 2PF_6^\ominus$ It is basically possible to separate the mixture into stereoisomers by known methods so that optically active bis-phosphonium salts are obtainable in this manner. These salts, if used e.g. as phase transfer catalysts, are capable of producing an asymmetric induction of the reaction they catalyze.

EXAMPLE 1

Ethylene-1,2-bis(trimethylphosphonium-hexafluorophosphate)

0.70 g $(CH_3)_3P-CH_2$ (7.77 millimol) in 10 cm$^3$ tetrahydrofurane was added dropwise within 1 h at a temperature of −60° to −70° C. (while cooling with ethanol/dry ice) and with thorough agitation to a suspension of 1.1 g $CuCl_2$ (8.18 millimol) in 20 cm$^3$ tetrahydrofurane. After addition of the ylide, the reaction mixture was allowed gradually to assume room temperature and the whole was stirred for a further 2 hours. The resulting ocher-colored solid was suspended in 30 cm$^3$ $H_2O$ and stirred until it appeared colorless. This colorless precipitate was filtered off, dissolved in 10–20 cm$^3$ concentrated HCl and admixed with 1.27 g $NH_4PF_6$ (7.79 millimol) dissolved in 20 cm$^3$ $H_2O$ wile cooling with ice. The resulting product was filtered off, washed several times with HCl and water and recrystallized from water. A colorless air-stable solid which had a fusion point of 286° C. was obtained in a yield of 0.68 g (37.2% of the theoretical).

$C_8H_{22}F_{12}P_4$ (470.16) Calc.: C 20.44; H 4.72; Found: C 20.83; H 4.74

The structure of this compound was evidenced by NMR-spectra.

EXAMPLE 2

Ethylene-1,2-bis(triethylphosphonium-hexafluorophosphate)

2.58 g $(C_2H_5)_3P=CH_2$ (19.5 millimol) in 30 cm$^3$ tetrahydrofurane was added dropwise under the conditions described in Example 1 to a suspension of 3.35 g $CuCl_2$ (24.9 millimol) in 60 cm$^3$ tetrahydrofurane. The whole was allowed to assume room temperature and stirred for a further 2 hours. The resulting light green solid was thoroughly washed with water until it appeared colorless. The colorless precipitate was filtered off, dissolved in 50 cm$^3$ $CH_3CN$, admixed with 1 ml $H_2O_2$ and stirred for 12 hours in the open air. Green chlorocuprate(II) of the formula $[(C_6H_5)_3P-CH_2CH_2-P(C_6H_5)_3]^{2\oplus}$ $2[Cu(OH)Cl_2]^\ominus$ or $[CuCl_4]^{2\ominus}$ was found to precipitate from the solution. The compound was filtered off, dissolved in $H_2O$ while adding several drops of HCl, and admixed with 2.0 g $NH_4PF_6$ (12.3 millimol) dissolved in 10 cm$^3$ $H_2O$, while cooling with ice. The resulting colorless salt was washed with water and a little HCl and recrystallized from water. A colorless air-stable solid which had a fusion point of 210° C. was obtained in a yield of 1.63 g (30.2% of the theoretical).

$C_{14}H_{34}F_{12}P_4$ (554.32) Calc.: C 30.34; H 6.18; Found: C 30.93; H 6.17

The structure of this compound was evidenced by NMR-spectra.

EXAMPLE 3

Ethylene-1,2-bis(triphenylphosphonium-hexafluorophosphate)

The reaction was effected under the conditions of Example 1 using 0.85 g $CuCl_2$ (6.3 millimol) in 20 cm$^3$ tetrahydrofurane and 1.28 g $(C_6H_5)_3P=CH_2$ (4.6 millimol) in 10 cm$^3$ tetrahydrofurane. After stirring for 2 hours at room temperature, a yellow-colored product was obtained; it was dissolved in 10 cm$^3$ concentrated HCl and 20 cm$^3$ water and admixed with 0.75 g $NH_4PF_6$ (4.6 millimol) in 10 cm$^3$ $H_2O$, while cooling with ice. The resulting colorless salt was filtered off, washed with HCl and water and dried under vacuum at 100° C.; a colorless air-stable solid which had a fusion point of 208°–215° C. was obtained in a yield of 1.31 g (67.6% of the theoretical).

$C_{38}H_{34}F_{12}P_4$ (842.58) Calc.: C 54.17; H 4.07; Found: C 54.40; H 4.30.

The structure of this compound was evidenced by NMR-spectra.

EXAMPLE 4

1,2-dimethyl-ethylene-1,2-bis(triethylphosphonium-hexafluorophosphate)

2.3 g $CuCl_2$ (17.1 millimol) in 40 cm$^3$ tetrahydrofurane was reacted under the conditions described in Example 1 with 2.5 g $(C_2H_5)_3P=CHCH_3$ (17.1 millimol) in 20 cm$^3$ tetrahydrofurane. The colorless product obtained was filtered off, washed with tetrahydrofurane, dissolved in 15 cm$^3$ $CH_3CN$ and the solution was stirred for 24 hours in the open air. $CH_3CN$ which evaporated was replaced. The resulting green solid was filtered off, washed with $CH_3CN$ and dissolved in 10 cm$^3$ $H_2O$ containing a few drops of concentrated HCl. Next, a solution of 1.5 g $NH_4PF_6$ (9.2 millimol) in 2 cm$^3$ water was added while cooling with ice. A viscous product was initially obtained; after decantation of supernatant liquor and washing the product with water, it was crystalline. It was a colorless air-stable solid which had a fusion point of 102° C. and was obtained in a yield of 1.61 g (32.3% of the theoretical).

$C_{16}H_{38}F_{12}P_4$ (582.37) Calc.: C 33.00; H 6.58; Found: C 32.21; H 6.47

The structure of this compound was evidenced by NMR-spectra which also indicated that the solid so obtained consisted of optical antipodes of the RR/SS type on the one hand and of the RS-meso form on the other hand, in the molar ratio of 2.8:1.

We claim:

1. Bis-phosphonium salts of the general formula

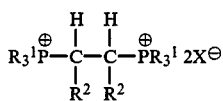

in which

R$^1$ is a member selected from the group consisting of methyl, ethyl, n-propyl, iso-propyl and butyl, R$^2$ is a member selected from the group consisting of methyl, ethyl, n-propyl and iso-propyl, and X$^\ominus$ is a member selected from the group consisting of a halide, dihalogenocuprate(I), tetraphenylborate, tetrafluoroborate and hexafluorophosphate, or 2X$^\ominus$ stands for a sulfate.

2. A process for making bis-phosphonium salts of the general formula

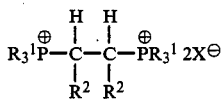

in which

R$^1$ is a member selected from the group consisting of methyl, ethyl, n-propyl, iso-propyl, butyl, a cycloalkyl having from 5–8 carbon atoms, and phenyl, R$^2$ is a member selected from the group consisting of a hydrogen radical, methyl, ethyl, n-propyl and iso-propyl, and X$^\ominus$ is a member selected from the group consisting of a halide, tetraphenylborate, tetrafluoroborate and hexafluorphosphate, or 2X$^\ominus$ stands for a sulfate, R$^1$ standing for a group other than a cycloalkyl or phenyl group in the event of R$^2$ standing for a radical other than a hydrogen radical, which comprises: reacting a triorganylphosphonium alkylide of the general formula $R_3^1P=CHR^2$ with an anhydrous copper (II)halide, the molar ratio of alkylide: halide being $\leq 1$, in a solvent at temperatures of $-78°$ C.–0° C. with agitation, and separating precipitated bis-phosphonium dihalogenocuprate(I).

3. A process as claimed in claim 2, wherein the separated bis-phosphonium-dihalogenocuprate(I) is subjected to a metathesis reaction with equivalent quantities of an alkali metal or ammoniumhexafluorophosphate and converted into a bis-phosphonium hexafluorophosphate.

4. A process as claimed in claim 2, wherein a solution of the triorganylphosphonium alkylide in an ether in a molar ratio of alkylide to CuHal$_2$ of at most 1 is slowly added dropwise with intense agitation at temperatures of $-78°$ C.–0° C. to a suspension of an anhydrous Cu-(II)-halide in an ether, the whole is allowed to assume room temperature while agitation is continued over a period of several hours, and precipitated bis-phosphonium-dihalogenocuprate(I) is filtered off and washed with water.

5. A process as claimed in claim 4, wherein the ether used is tetrahydrofurane, a dioxane or ethyleneglycol ether.

6. A process as claimed in claim 4, wherein the bis-phosphonium-dihalogenocuprate(I) filtered off and washed in subjected to a metathesis reaction with equivalent quantities of an alkali metal or ammoniumhexafluorophosphate and converted into a bis-phosphonium hexafluorophosphate.

7. A process as claimed in claim 6, wherein bis-phosphonium-hexafluorophosphate is made by filtering off precipitated bis-phosphonium-dihalogencuprate(I), washing it with water, dissolving it in concentrated hydrochloric acid, admixing it, while cooling with ice, with an aqueous solution of an alkali metal or ammoniumhexafluorophosphate, filtering off precipitated bis-phosphoniumhexafluorophosphate and washing it with hydrochloric acid and water.

8. A process as claimed in claim 6, wherein bis-phosphonium-hexafluorophosphate is made by filtering off precipitated bis-phosphonium-dihalogenocuprate(I), washing it with water, dissolving it in acetonitrile, stirring it with admission of air, filtering off precipitated bis-phosphonium-halogenocuprate(II), dissolving it in water while adding hydrochloric acid, admixing it, while cooling with ice, with an aqueous solution of an alkali metal or ammoniumhexafluorophosphate, separating the resulting bis-phosphonium-hexafluorophosphate and washing it with water and hydrochloric acid.

9. A process as claimed in claim 8, wherein the bis-phosphonium-halogenocuprate(I) filtered off and washed with water is admixed with hydrogen peroxide and stirred with admission of air.

* * * * *